United States Patent [19]
Irani

[11] Patent Number: 5,405,370
[45] Date of Patent: Apr. 11, 1995

[54] AIR BLANKET

[76] Inventor: Feraidoon Irani, 8421 Schoolgate Dr., Huber Heights, Ohio 45424

[21] Appl. No.: 173,770

[22] Filed: Dec. 22, 1993

Related U.S. Application Data

[63] Continuation-in-part of Ser. No. 956,837, Oct. 5, 1992, abandoned, which is a continuation of Ser. No. 790,581, Nov. 8, 1991, abandoned.

[51] Int. Cl.$^6$ .............................................. A61F 7/00
[52] U.S. Cl. ........................................ 607/104; 607/114
[58] Field of Search ................... 128/96, 104, 108–112, 128/114; 165/46; 264/283

[56] References Cited

U.S. PATENT DOCUMENTS

| | | |
|---|---|---|
| 2,093,834 | 4/1934 | Gaugler . |
| 2,110,022 | 3/1938 | Kliesrath . |
| 2,235,966 | 3/1941 | Summers . |
| 2,512,559 | 6/1950 | Williams . |
| 2,601,189 | 6/1952 | Wales, Jr. . |
| 2,991,627 | 7/1961 | Suits . |
| 3,468,299 | 9/1969 | D'Amato .................... 607/104 X |
| 3,867,939 | 2/1975 | Moore et al. . |
| 3,879,257 | 4/1975 | Gentile et al. . |
| 4,151,658 | 5/1979 | Hibino et al. . |
| 4,540,412 | 9/1985 | Van Overloop . |
| 4,572,188 | 2/1986 | Augustine et al. . |
| 4,660,388 | 4/1987 | Greene, Jr. . |
| 4,753,241 | 6/1988 | Brannigan et al. .................. 607/112 |
| 4,777,802 | 10/1988 | Feher . |
| 4,867,230 | 9/1989 | Voss ................................ 607/104 X |
| 5,044,364 | 9/1991 | Crowther . |
| 5,106,373 | 4/1992 | Augustine et al. .............. 607/104 X |
| 5,125,238 | 6/1992 | Ragan et al. . |
| 5,168,589 | 12/1992 | Stroh et al. . |
| 5,184,612 | 2/1993 | Augustine . |
| 5,304,213 | 4/1994 | Berke et al. . |

Primary Examiner—Angela D. Sykes
Attorney, Agent, or Firm—Biebel & French

[57] ABSTRACT

An inflatable air blanket of the type adapted to treat hypothermia and the like is disclosed. The blanket comprises an air barrier layer, substantially impervious to airflow, and an underlying heat transfer layer adapted to permit penetration and diffusion of air therethrough. The barrier layer and heat transfer layer are joined together to form an envelope or chamber adapted for reception of warm air. The heat transfer layer may comprise a laminate-like non-woven web structure with outer layers thereof including a bonding material disposed in a reticular pattern thereon. Air from the envelope or chamber penetrates and uniformly diffuses through the heat transfer layer to gently impinge upon the treated patient.

26 Claims, 8 Drawing Sheets

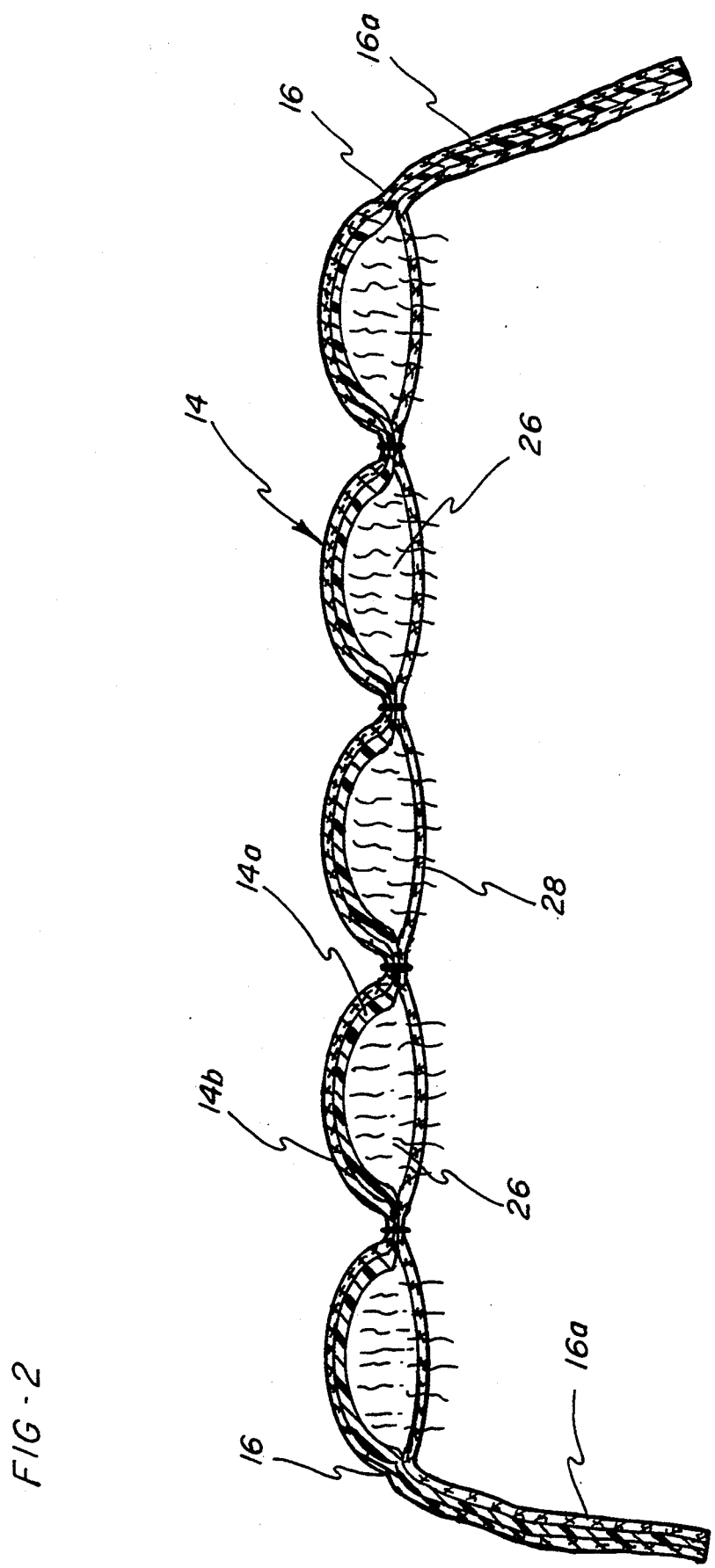

AIR BLANKET

CROSS-REFERENCE TO RELATED APPLICATIONS

This application is a continuation-in-part of co-owned U.S. application Ser. No. 07/956,837, filed Oct. 5, 1992, which is a file wrapper continuation of U.S. Ser. No. 790,581, filed Nov. 8, 1991, both now abandoned.

FIELD OF THE INVENTION

The present invention pertains to a disposable, inflatable blanket structure that is adapted for reception of heated or cooled air to control the body temperature of a patient.

BACKGROUND OF THE INVENTION

Regulation of a patient's body temperature as a result of surgery, heat prostration, hypothermia, or other conditions, is often required. Heat transfer blankets or covers, such as those disclosed in U.S. Pat. No. 2,110,022 (Kleisrath), have been suggested wherein a heat transfer fluid is circulated throughout a composite fabric in coils or conduits disposed throughout the fabric or quilt matrix. For example, in the '022 patent disclosure, the coils wind through a composite fabric composed of a wool blanket top layer and a heat conducting blanket layer formed from cotton, linen, silk, etc.

In another embodiment of U.S. Pat. No. 2,110,022, a woolen blanket upper layer is disposed over a bag formed from rubber or similar flexible material. Cooling air is forced into the bag and exits over the patient through a plurality of discrete openings in the bottom bag side.

Another airflow device is disclosed in U.S. Pat. No. 4,572,188 (Augustine et al) wherein the airflow cover comprises a parallel array of longitudinally arranged, inflatable, plastic tubes that are joined together along lengthwise sides. Transverse, connecting channels are provided in the tubes so that a thermally controlled gas mixture introduced through an entry port, fills the tubes and exits over the patient through a series of exit ports on the flattened bottom side of the tube array.

As sold commercially, the manufacturer of the '188 device suggests that it be used in combination with an overlying surgical drape. Moreover, due to the plurality of discrete openings in the bottom flattened portions of the parallel plastic tubes, air emanating from the tubes jets across the patient at a plurality of distinct locations in contradistinction to uniform and gentle diffusion of the heating (or cooling) medium over the entirety of the covered surface.

Another approach to the problem is disclosed in U.S. Pat. No. 5,044,364 (Crowther). In this device, a plurality of arch-shaped air pockets are provided 9 transversely spanning the treated patient. Openings between adjacent air pockets allow inflation air to flow from one pocket to the next until the pockets are fully inflated. A separate air chamber is disposed underneath the transverse arch-shaped pockets and is provided with a plurality of perforations therein allowing air to flow continuously over the treated patient.

SUMMARY OF THE INVENTION

In accordance with the invention, an inexpensive, disposable air blanket is provided that can be used to regulate the body temperature of a treated patient. Contrary to prior art devices, the inflatable air blanket of the invention does not require additional use of an overlying surgical drape or blanket. Moreover, upon inflation, the air blanket softly floats over the patient providing a space of less than 1" between the blanket and patient. Some of the prior art blankets float atop and are separated from the patient by as much as 5"-6".

Most importantly, unlike prior art devices, the air blanket of the invention provides for uniform penetration of the heat transfer air, usually warm air, into the heat transfer layer adjacent the patient. Further, as opposed to jetting of the air across the patient in a plurality of discrete streams, air softly and uniformly diffuses through the heat transfer layer to gently impinge upon the patient.

The heat transfer layer of the present blanket is composed of a unitary laminate-like, non-woven fibrous web material. The laminate-like material comprises a central fibrous containing core composed essentially of a web of staple cellulosic textile and paper making fibers. On either side of the core, a reinforced, abrasion resistant fiber containing surface region is provided. These surface regions or layers comprise a bonding material thereon disposed in a finely spaced pattern, such as a reticular or diamond-like pattern. The bonding material bonds the fibers into a strong network and forms a net-like outer web over the core to impart additional strength to the structure.

The present invention will be further described in conjunction with the following detailed description and appended drawings.

BRIEF DESCRIPTION OF THE DRAWINGS

FIG. 2 is a cross-sectional view of the air blanket taken along the lines and arrows 2—2 of FIG. 1;

DETAILED DESCRIPTION OF A PREFERRED EMBODIMENT

Figure 1:
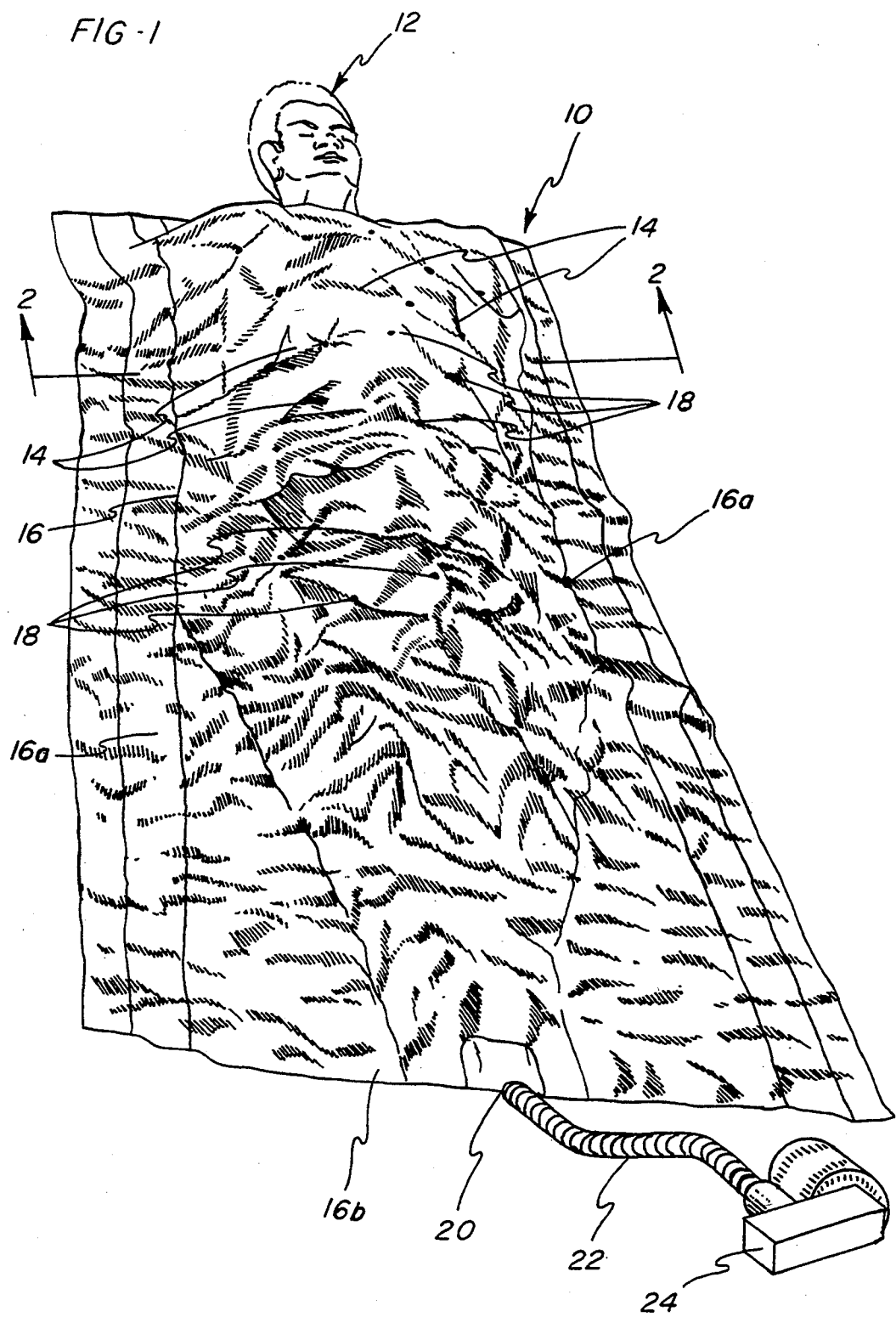
FIG. 1 is a perspective view of the air blanket in accordance with the invention shown disposed over a patient.

Turning now to the drawings, and specifically to FIG. 1 thereof, there is shown air blanket 10 of the invention. The air blanket 10 is superposed over patient 12 for the purpose of providing temperature adjusted air such as either cooling or warming air thereto and extends along and covers the entire length of the patient.

Although the invention will be further described with reference to provision of heated air in the blanket to provide warming treatment to the patient as desirable in treating hypothermia or in conjunction with a variety of surgical procedures, it is to be noted that the blanket could just as easily be inflated with cool air from a refrigeration unit, etc.

As shown, warm air from heater-blower assembly 24 is pumped into entry port 20 of blanket 10 through connecting hose 22 which can be provided with a clamp (not shown) to seal flow of air into the blanket.

Blanket 10 comprises a rectangularly-shaped upper or barrier layer 14 formed of an air impermeable material, sealed around substantially the entire peripheral or border area of the blanket to underlying lower or heat transfer layer 28 (FIG. 2) formed of an air permeable material, as shown at 16, in order to form an envelope or chamber for reception of air from heater-blower assembly 24 within the blanket area circumscribed by the sealing means 16.

A plurality of stitches or other distinct connection points 18 are formed attaching the barrier layer 14 to the heat transfer layer 28 at a plurality of locations within the interior boundary of the blanket circumscribed by the heat seal means 16. Accordingly, the air chamber between the barrier layer and heat transfer layer forms a plurality of quilt-like pockets.

The seals 16, preferably heat seals although other sealing means may be used, extend longitudinally and transversely with respect to the length of blanket 10 to provide longitudinally disposed, non-inflatable zones 16a and transversely disposed non-inflatable zones 16b bordering the blanket that aid in maintaining the blanket in close but not touching relation to the treated patient. Air entry into zones 16a and 16b is impeded by the heat seals 16. Since air from port 22 does not enter into these zones, the effective density of each of the zones is made greater than that of the air pockets (see FIG. 2). The zones 16a, 16b thus, upon inflation of the blanket, have a tendency to bend slightly toward the patient, sealing the patient from the ambient atmosphere and providing floating of the blanket spaced closely (i.e., less than 1") over the patient.

In FIG. 2, air envelope or pockets 26 are shown. As shown, these air pockets 26 are defined as the areas bordered by the connection points 18 or by the seals 16 and the connection points 18. The barrier layer 14 includes a two-ply laminate structure including lower, air impervious layer 14a preferably composed of a plastic or plastic coated material and an upper layer 14b formed from an insulative material, such as paper fibers or textile fabric. Also, longitudinally extending noninflatable zones 16a, 16a, are shown curving downwardly, as previously explained, adapted to cover the sides of the treated patient.

The lower layer 28 is preferably a uniformly porous material and may be a porous laminate-like fibrous web material that serves as a heat transfer layer which is to be positioned over the patient. Air from the pockets 26 diffuses substantially uniformly through the heat transfer layer 28 to gently impinge upon the treated patient substantially uniformly over the entire surface covered by the blanket.

Figure 3A:
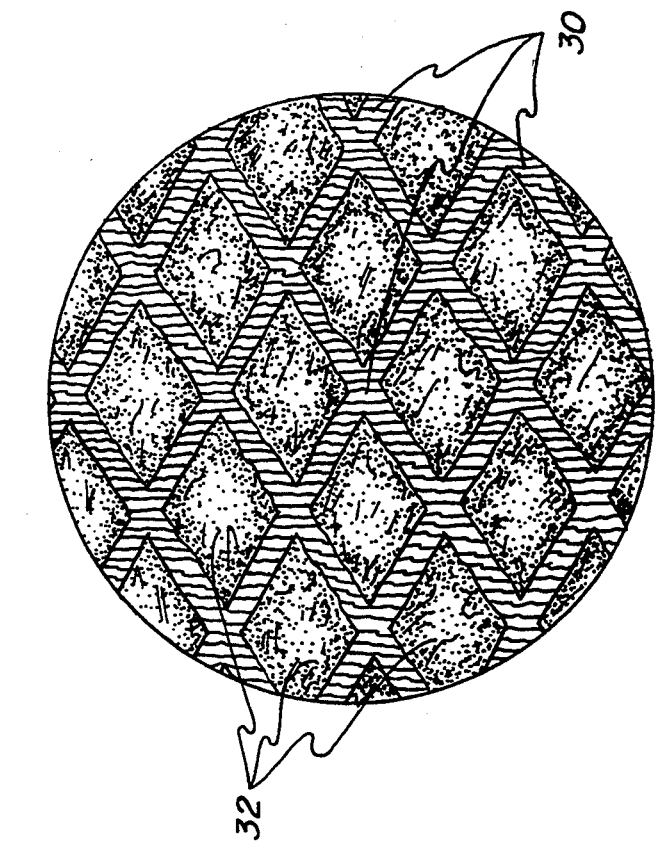
FIG. 3A is a magnified view of a portion of the heat transfer layer shown in FIG. 3.
Figure 3:
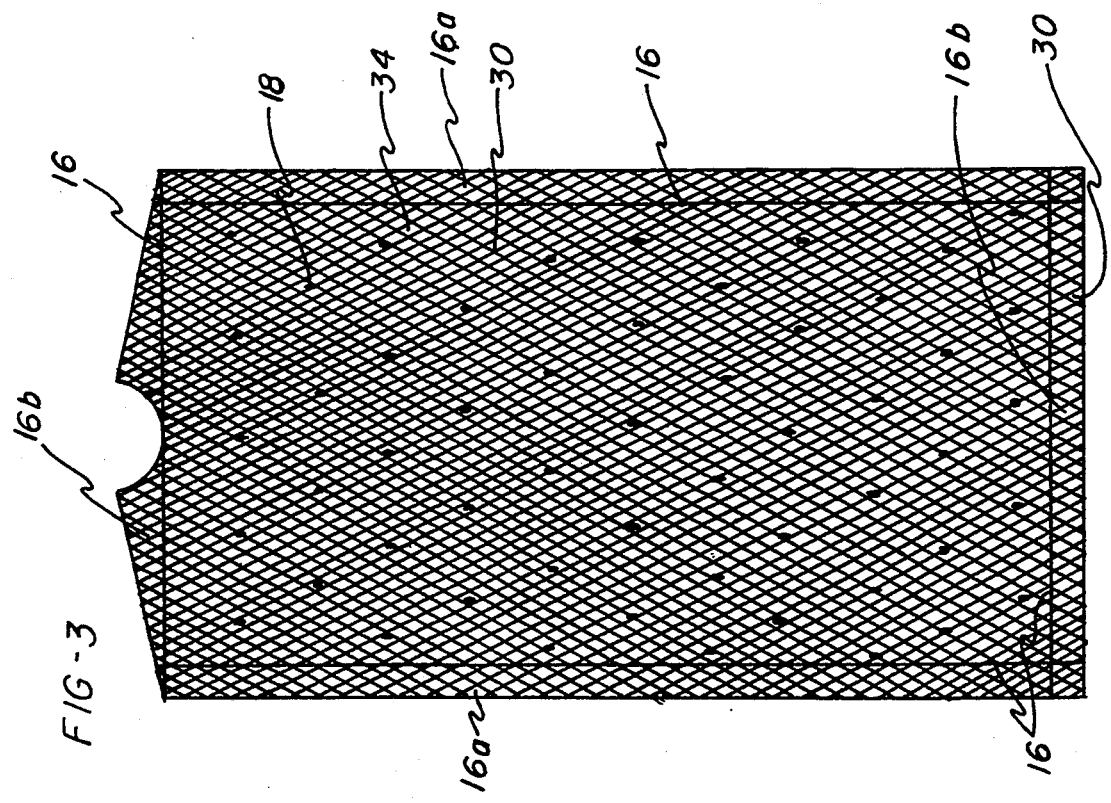
FIG. 3 is a bottom, plan view of the air blanket, showing the heat transfer layer that is adapted for positioning adjacent the patient.

FIGS. 3 and 3A depict the bottom surface of heat transfer layer 28 that is to be positioned on top of the patient. The heat transfer layer comprises a non-woven fibrous core 32 including a surface layer 34 exhibiting a reticulated or net-like pattern formed by bonding material 30 imparted to both sides of the fibrous core 32 (only one such side is shown in FIGS. 3 and 3A).

With specific reference to FIG. 3A, the reticulated or net-like pattern formed from bonding material 30 in the surface layer is provided over fibrous core 32 and provides for web strength and integrity. The bonding material binds together individual fibers from the core 32 and the surface layer 34 containing the bonding material. Provision of the bonding material in a net-like or reticulated pattern, as shown, imparts enhanced strength and structural integrity to the heat transfer layer 28. Fibrous core 32 comprises a multiplicity of staple paper making and/or textile fibers.

The heat transfer layer 28 may comprise a unitary laminate-like fibrous web of the type described in detail in U.S. Pat. No. 3,879,257 (Gentile et al), the disclosure of which is hereby incorporated by reference herein. Commercial products made in accordance with this disclosure are available from Scott Paper Company, Delaware County, Pa., under a variety of designations, such as Scottcloth 05720, 05730, 05930, 05940 or 3855-0.

Figure 4:
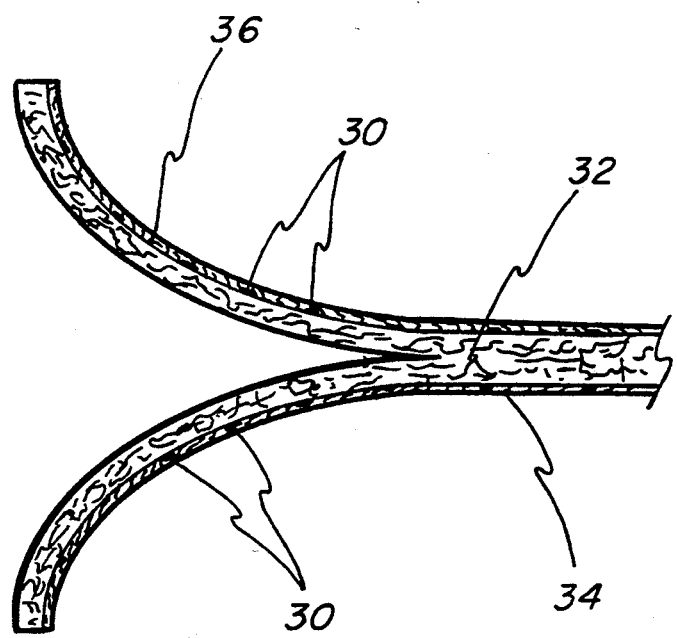
FIG. 4 is a diagrammatical illustration, showing the construction of the heat transfer layer with the central core region of the heat transfer layer of the blanket peeled into two portions.

In accordance with the '257 disclosure, and in regard to FIG. 4, the soft, absorbent heat transfer layer 28 has three laminate-like regions. A soft central core region 32 is sandwiched between two surface regions 34, 36. Each surface region is treated with a bonding material 30 as previously described that aids in binding the fiber constituents of the core 32 and surface layers 34, 36 into a strong network. The bonding material also imparts abrasion resistance to both parts of the web. As shown in FIGS. 3 and 3A, the bonding material is provided in a reticular or net-like pattern. However, although the reticular or net-like pattern is preferred, other patterns, such as fine lines, dots, etc., may be used. As the '257 patent indicates, it is preferred that the bonding material 30 occupies between about 15–60% of the surface area of the web.

The web consists principally of cellulosic paper making fibers and can be modified so as to include longer staple synthetic rayon fibers therein. As per the examples of the '257 patent, a non-woven base web is formed on conventional paper making equipment from a pulp slurry of 90% bleached sulfate soft wood (dry lap) and 10% uncrimped ¼ staple 1.5 d rayon. Sizes, such as quarternized imadazolines, can be used, if desired, to control the amount of interfiber finding of the paper making fibers. The base web may then be dried in conventional manner, such as with a yankee dryer. The bonding material, in the desired pattern, may be imparted to opposing sides of the base web by rotogravure rolls with the opposing web sides being creped subsequent to application of the bonding material.

At present, the preferred material for the heat transfer layer 28 is available from Kimberly-Clark under the "S.M.S." trademark. It is a non-woven fibrous web material composed of polypropylene fibers. Another exemplary material that may be used as the layer 28 is available under the "KLEENGUARD" trademark from Kimberly-Clark. This latter material is also a non-woven fibrous web composed of polyolefinic fibers.

The bonding material can comprise any one of a host of materials, such as acrylate emulsions, vinyl acetate, vinyl chloride, methacrylate based resins, water soluble resins, such as the carboxymethyl cellulose ethers, polyvinyl alcohol emulsions or polyacrylamides. Most preferably, the binding material includes an elastomeric component, such as butadiene-styrene, neoprene, polyvinyl chloride polymers, sundry vinyl copolymers, nylons, etc.

Due to the penetration of the bonding material into the web, it bonds at least some of the fibers together to form bonded web portions located throughout the surface regions of the web.

Especially preferred for use as the heat transfer layer are the web-like laminates having basis weights of between about 20–100 pounds per ream of 2,880 square feet. The bonding material extends from about 10 to 60% through the thickness of the entire web with the bonding material applied to one surface layer being substantially unconnected to the bonding material extending into the web from the other side of the web.

It is highly advantageous and readily apparent from the above that the heat transfer layer 28, due to its fibrous web construction, captures or retains heat from the air chamber and then diffusively circulates same over the treated patient.

Figure 5:
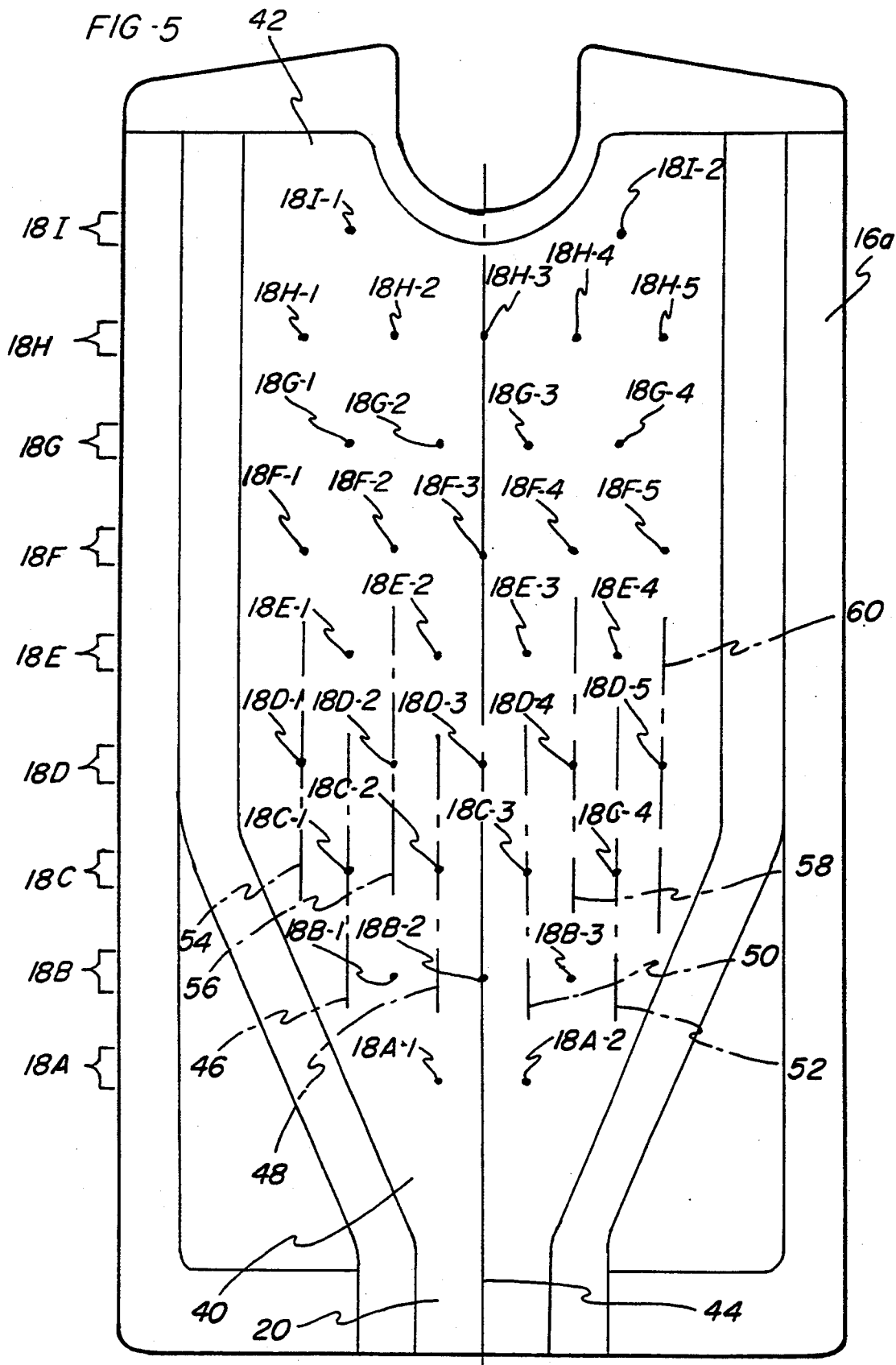
FIG. 5 is a top plan view of the blanket identifying the particular locations of the connection points between the top and bottom layers.
Figure 6:
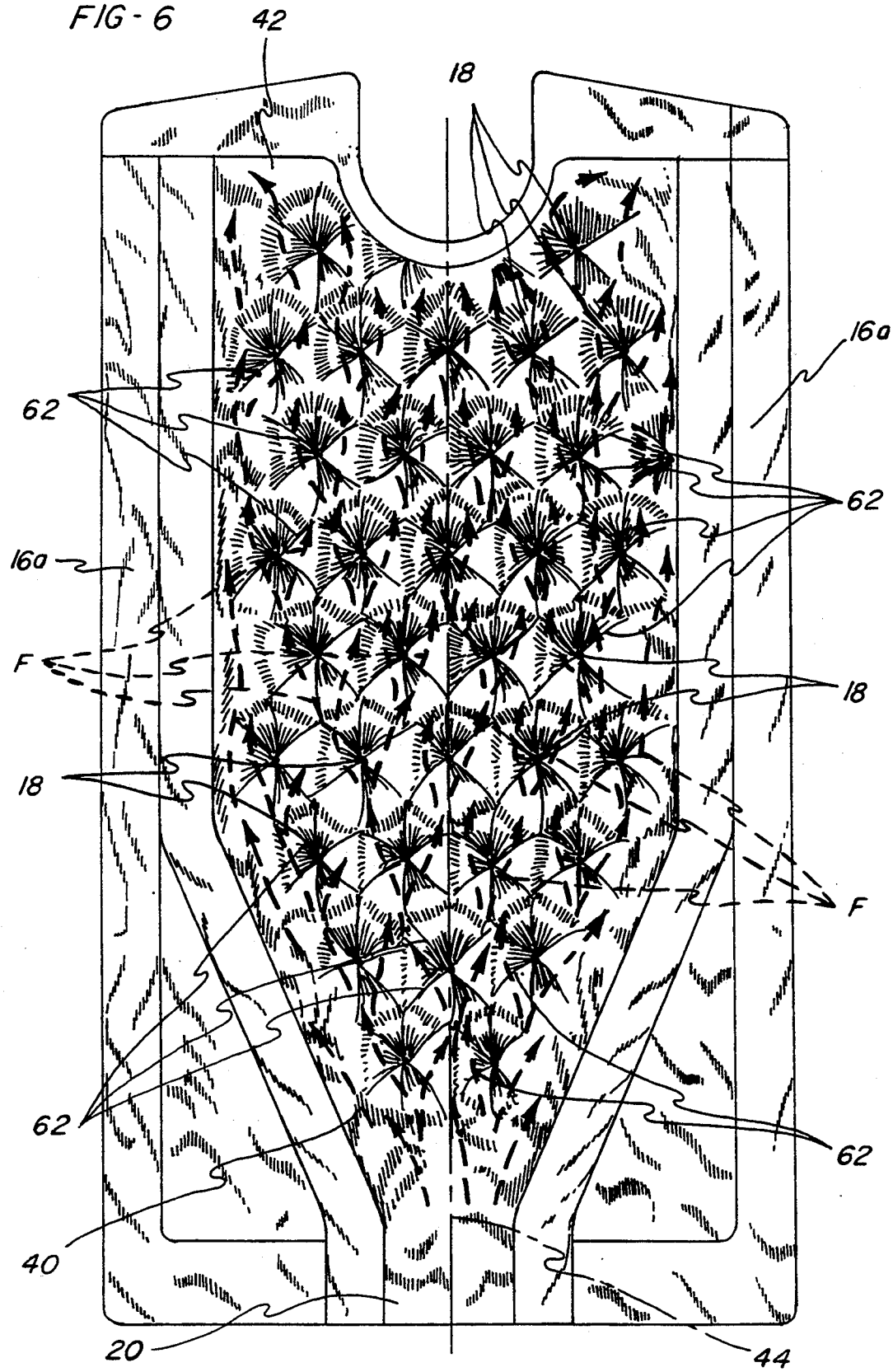
FIG. 6 is a top plan view of the blanket illustrating the partitions formed by the connecting points and the resulting airflow directions within the air chamber of the blanket.

Referring to FIGS. 5 and 6, the operation of the present blanket 10 will be described with further reference to the specific locations of the distinct connection points 18 within the air chamber defined by the peripheral connection 16 between the upper barrier layer 14 and the lower heat transfer layer 28. The locations of the connection points 18 are selected such that a substantially uniform temperature throughout the air chamber is obtained for the temperature adjusted air introduced into the air chamber of the blanket 10.

It should be noted that, in the absence of the connection points 18 at the locations shown, warm air introduced into the blanket 10 through the port 20 would rush to a distal end 42 of the blanket opposite from the end where the entry port 20 is located due to the porous nature of the lower layer 28 permitting a high flow rate out of the blanket. Further, such a high airflow rate would result in the air at the distal end 42 establishing a warmer steady state temperature than the end 40 proximal to the entry port 20 such that the air diffusing on a patient through the lower layer 28 will exhibit a non-uniform temperature distribution across the surface area of the lower layer 14.

Accordingly, the connection points 18 are arranged to slow the airflow and to increase turbulence and mixing of the air as it passes from the proximal end 40 to the distal end 42 of the blanket 10. Specifically, as is illustrated in FIG. 5, the points 18 are arranged substantially in rows 18A-I which are configured in a laterally staggered pattern. Each connection point location is identified by its row location 18A-I in combination with a number designator indicating its location in the row. For example, row 18A includes connection points 18A-1 and 18A-2, and the connection points 18 of the next adjacent row 18B are identified as 18B-1, 18B-2 and 18B-3.

The blanket 10 defines a longitudinal axis 44 extending from the proximal end 40 to the distal end. 42 generally centrally between the side portion 16a of the blanket 10. The connection points 18 in adjacent ones of the rows 18A-I are staggered relative to each other in a lateral direction to thereby define angled flow paths for the air as it passes through the air chamber, as is indicated by the airflow arrows F in FIG. 6. In other words, each connection point 18 defines a location for a hypothetical longitudinal line passing through a respective connection point 18 parallel to said longitudinal axis 44 wherein a majority of longitudinal lines for each row 18A-I (FIG. 5) are laterally displaced relative to each of the longitudinal lines of an adjacent row. For example, the connection points 18C-1, 18C-2, 18-C3 and 18C-4 of row 18C define hypothetical longitudinal lines 46, 48, 50 and 52, respectively. The connection points 18D-1, 18D-2, 18D-4 and 18D-5 of the adjacent rows 18D define respective longitudinal lines 54, 56, 58, 60, with point 18D-3 lying on the longitudinal axis line 44. The longitudinal lines 46, 48, 50 and 52 pass substantially midway between adjacent pairs of longitudinal lines 54 and 56, 56 and 44, 44 and 58, and 58 and 60, respectively. The longitudinal lines defined by the other rows of connection points 18 are similarly related to the longitudinal lines of the respective immediately adjacent rows.

It should be noted that as a result of the above-described configuration for the location of the connection points 18, the upper layer 14 defines partitions 62 (FIG. 6) extending downwardly toward the lower layer 28 and extending in an oblique or diagonal direction, relative to the longitudinal axis 44, away from the connection points 18. Thus, it may be seen that as the air passes through the air chamber between two adjacent connection points 18 in each row, for example points 18C-1 and 18C-2, it will impinge on a connection point, such as 18D-2, and the associated diagonal partitions 62 in the next adjacent row. As the air impinges on the connection points 18 and partitions 62 in this manner, some of the air will be deflected back against the flow direction to create eddy currents, and other portions of the air will be deflected in a sideways direction. The net result of the connection points 18 causing the air to change its direction is that the turbulence and mixing of the air within the air chamber is increased, and the momentum of the flow of air toward the distal end 42 is substantially decreased. This result is critical to the operation of the blanket 10 of the present invention in that it prevents the warmed air from rushing to the distal end 42 in an uncontrolled manner and further ensures that the air temperature throughout the air chamber is substantially uniform through controlled deflection and mixing of the air.

It should be noted that although the position of the connection points 18 has been described in terms of points spaced substantially equally across the rows 18A-F, the spacing may be varied within the teaching of the present invention to the extent that the connection points are staggered such that air passing between connection points in one row will directly impinge upon connection points in a succeeding row to cause the air to deflect and mix. Further, a certain limited number of the connection points 18 shown in FIGS. 5 and 6 may be eliminated in order to adjust the amount of warm airflow reaching the distal end 42. For example, the connection points 18B-2, 18D-3, 18F-3, and 18H-3 located on the longitudinal axis 44 may be eliminated to increase the amount of warm air supplied to the distal end 42 while the remaining connection points 18 provide for effective mixing of the air to ensure that an adequate amount of warm air is retained at the proximal end 40 to produce a substantially uniform temperature distribution throughout the air chamber.

Figure 7:
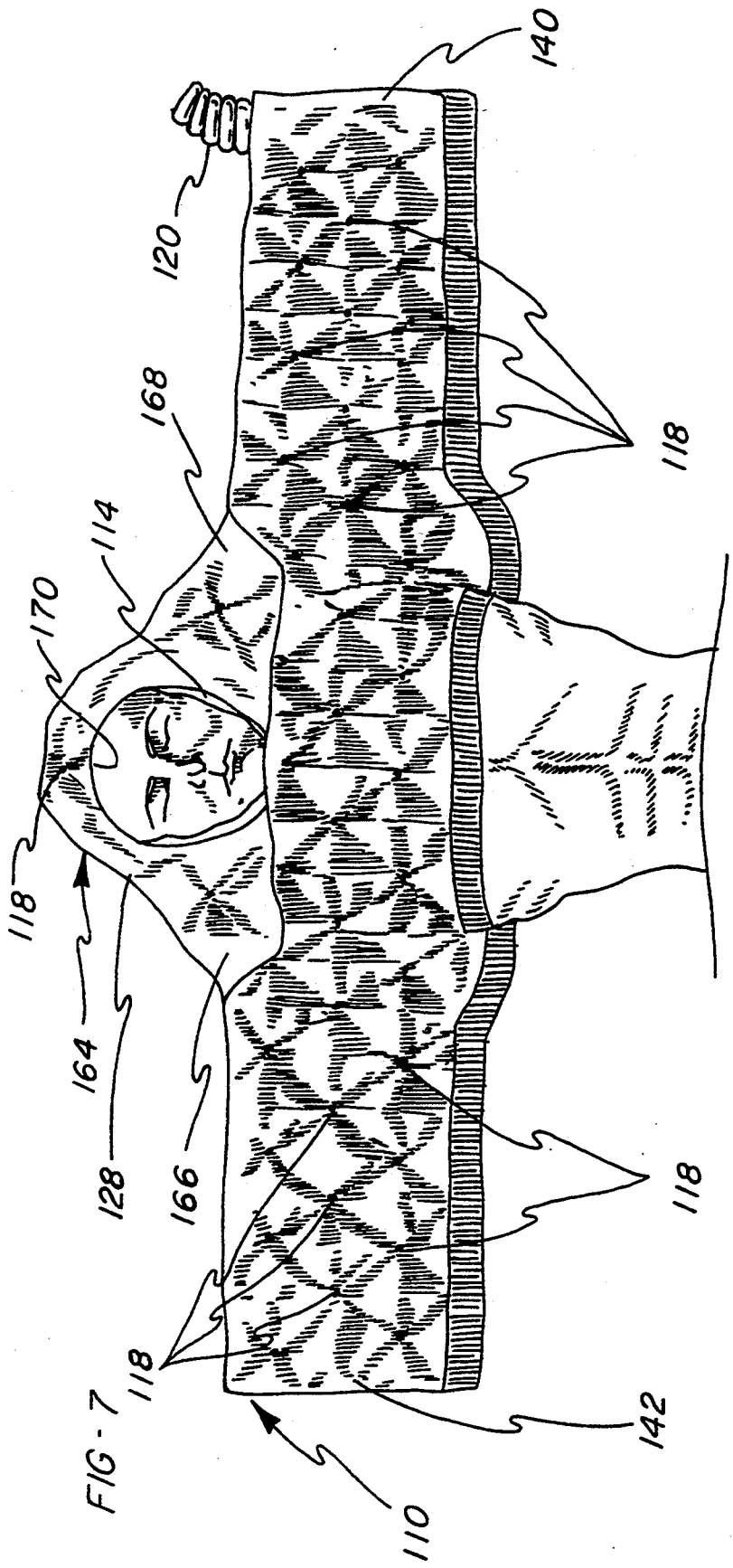
FIG. 7 illustrates a further embodiment of the blanket including a hood portion for a patient's head.

Referring to FIG. 7, a further embodiment of the invention is illustrated showing the use of the present blanket to warm the head and upper torso of a patient. The blanket 110 of this embodiment includes staggered connection points 118 as in the previous embodiment to control the airflow from a proximal end 140 adjacent to an air inlet portion 120 to a distal end 142. In addition, a hood 164 is provided for surrounding the head of a patient. The hood 164 includes opposing ends 166 and 168 which are attached to the main portion of the blanket 110 and which are in fluid communication with the air chamber of the blanket 110. The hood 164 includes an inner edge 170 defining an aperture opening for the patient's face and is constructed with an air impermeable outer layer 128 and an air permeable inner layer 114 whereby warmed air may be provided to both a patient's head and upper torso during a surgical operation.

Figure 8:
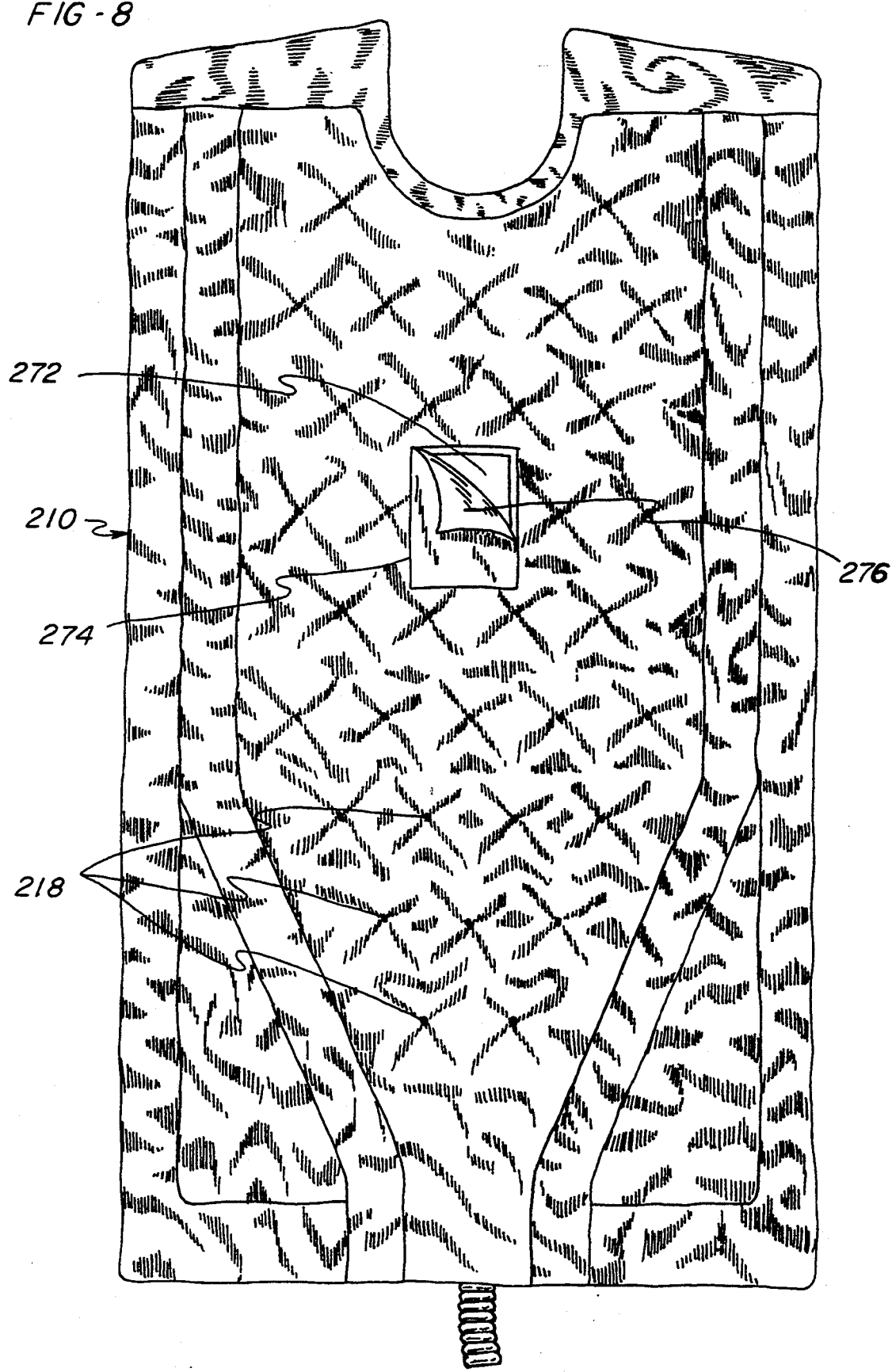
FIG. 8 illustrates yet another embodiment of the invention including an aperture for facilitating access to a patient during surgery.

FIG. 8 illustrates a further embodiment of the blanket of the present invention which may be used in a surgical operation. In this embodiment, the blanket 210 is formed with staggered connection points 218 arranged the same as in the first embodiment, and further includes an aperture 272 defined for example in a central portion of the blanket 210. The aperture 272 is defined by sealed edges 274 connecting the upper and lower layers of the blanket in sealed relation, and the sealed edges 274 may be provided with a fastening tape to fasten the blanket to the torso of a patient. In addition, the blanket may be supplied with the aperture 272 covered by a removable flap 276. The blanket 210 would preferably be sterilized to be used as a surgical draping wherein the aperture 272 provides access through the blanket 210 to perform a surgical operation on a patient. Thus, it can be seen that the blanket 210 eliminates the need to provide a separate warming blanket and draping material for a surgical operation, and is adapted to supply warmed air to an area immediately surrounding a surgery site.

Although the invention has been describe with respect to certain preferred embodiments, it will be appreciated that a wide variety of equivalents may be substituted for those specific elements shown and described herein, all without departing from the spirit and scope of the invention as defined in the appended claims.

What is claimed is:

1. A blanket for positioning over a patient to supply temperature adjusted air to said patient, said blanket comprising:
   an upper layer formed of an air impermeable material;
   a lower air permeable layer formed of a non-woven, fibrous material substantially free of discrete openings wherein temperature adjusted air may readily diffuse through said lower layer;
   a peripheral connection extending around and joining said upper layer and said lower layer to define an air chamber;
   an inlet port for supplying said temperature adjusted air to said air chamber; and
   wherein said upper layer defines partitions located in said air chamber to increase turbulence and mixing of said temperature adjusted air flowing through said air chamber where said temperature adjusted air will have a substantially uniform temperature distribution throughout said air chamber.

2. The blanket as in claim 1 wherein said partitions are defined by folds in said upper layer extending downwardly toward said lower layer.

3. A blanket for positioning over a patient to supply temperature adjusted air to said patient, said blanket comprising:
   an upper layer formed of an air impermeable material;
   a lower layer formed of an air permeable material wherein temperature adjusted air may readily diffuse through said air permeable material;
   a peripheral connection extending around and joining said upper layer and said lower layer to define an air chamber
   an inlet port for supplying said temperature adjusted air to said air chamber;
   said upper layer including folds defining partitions located in said air chamber; and
   wherein said blanket includes opposing proximal and distal ends and side portions extending between said ends, and a longitudinal axis is defined extending between said ends generally centrally between said side portions wherein said folds extend across said upper layer diagonally relative to said longitudinal axis to increase turbulence and mixing of said temperature adjusted air flowing through said air chamber whereby said temperature adjusted air will have a substantially uniform temperature distribution throughout said air chamber.

4. The blanket as in claim 3 including a plurality of distinct connection points between said upper layer and said lower layer wherein said folds extend from said distinct connection points.

5. The blanket as in claim 4 wherein said distinct connection points are arranged in rows extending laterally relative to said longitudinal axis, each said connection point defining a location for a longitudinal line passing through a respective connection point parallel to said longitudinal axis, at least one of said longitudinal lines of each row being laterally displaced relative to each of said longitudinal lines of an adjacent row.

6. A blanket for positioning over a patient for supplying temperature adjusted air to said patient, said blanket comprising:
   an upper layer formed of an air impermeable material;
   a lower layer formed of a substantially uniformly porous air permeable material wherein temperature adjusted air may readily diffuse through said air permeable material;
   a peripheral connection extending around and joining said upper layer and said lower layer to define an air chamber;
   opposing proximal and distal ends and side portions extending between said ends;
   an inlet port located at said proximal end for supplying said temperature adjusted air to said air chamber;
   a longitudinal axis defined by said upper and lower layers extending from said proximal end to said distal end generally centrally between said side portions;
   a plurality of distinct connection points between said upper and lower layers arranged substantially in rows extending laterally of said longitudinal axis; and
   wherein said connection points in adjacent rows are staggered relative to each other in a lateral direction to thereby define angled airflow paths through said air chamber such that a substantially uniform temperature distribution for said temperature adjusted air will be obtained throughout said air chamber.

7. The blanket as in claim 6 wherein each connection point defines a location for a longitudinal line passing through a respective connection point parallel to said longitudinal axis and at least one of said longitudinal lines of each row is laterally displaced relative to each of said longitudinal lines of an adjacent row.

8. The blanket as in claim 7 wherein a majority of said longitudinal lines of each row are laterally displaced relative to each of said longitudinal lines of an adjacent row.

9. The blanket as in claim 7 wherein said longitudinal lines of at least one of said rows are located substantially midway between adjacent ones of said longitudinal lines of an adjacent row.

10. The blanket as in claim 6 including partitions defined by said upper layer, said partitions extending from said distinct connection points diagonally relative to said longitudinal axis to control airflow from said proximal end to said distal end.

11. In a blanket for diffusing temperature-adjusted air to a patient over which said blanket is positioned, including an upper, air impermeable layer, a lower, air permeable layer through which temperature-adjusted air may be diffused, means forming a peripheral connection between said upper and lower layers and defining an air chamber, and means for supplying temperature-adjusted air to said air chamber, the improvement comprising:
said lower layer being formed of a non-woven, fibrous material substantially free of discrete openings.

12. The blanket as in claim 11 further comprising:
bonding material applied to said non-woven fibrous material.

13. The blanket as in claims 12 wherein said bonding material occupies between about 15 to 60 percent of the surface area of said lower layer.

14. The blanket as in claim 12 wherein said bonding material is applied to said non-woven fibrous material in a discontinuous pattern.

15. The blanket as in claim 14 wherein:
said bonding material is applied to said non-woven fibrous material in a substantially reticular pattern.

16. The blanket as in claim 14 wherein:
said bonding material is applied to opposite surfaces of said non-woven fibrous material.

17. The blanket as in claim 16 wherein:
said bonding material is supplied to said non-woven fibrous material in a substantially net-like pattern.

18. The blanket as in claim 11 wherein:
said non-woven fibrous material comprises cellulosic fibers.

19. The blanket as in claim 18 wherein:
said cellulosic fibers comprise paper fibers.

20. The blanket as in claim 11 wherein:
said non-woven fibrous layer comprises synthetic fibers.

21. The blanket as in claim 20 wherein:
said non-woven fibrous material comprises polypropylene fibers.

22. The blanket as in claim 20 wherein:
said non-woven fibrous material comprises polyolefinic fibers.

23. The blanket as in claim 11 further comprising:
means for generating turbulence in said air chamber.

24. The blanket as in claim 11 further comprising:
means for generating eddy currents in said air chamber.

25. The blanket as in claim 11 wherein said lower layer is in direct fluid communication with said air chamber and defines a lower outer surface for said blanket.

26. In a blanket for diffusing temperature-adjusted air to a patient over which said blanket is positioned, including an upper, air impermeable layer, a lower, air permeable layer through which temperature-adjusted air may be diffused, means forming a peripheral connection between said upper and lower layers and defining an air chamber, and means for supplying temperature-adjusted air to said air chamber, the improvement comprising:
said lower layer being formed of three laminate-like regions defining a non-woven fibrous material substantially free of discrete openings and including:
a soft central core of non-woven fibrous material; and
bonding material applied to opposite surfaces of said soft central core in a reticular pattern occupying between about 15–60 percent of the surface area of said soft central core; and
means for generating turbulence within said air chamber.

* * * * *